United States Patent
Biggs

Patent Number: 6,030,360
Date of Patent: Feb. 29, 2000

[54] STEERABLE CATHETER

[76] Inventor: Robert C. Biggs, 1005 Alderman Dr. Suite 101, Alpharetta, Ga. 30202

[21] Appl. No.: 08/777,548

[22] Filed: Dec. 30, 1996

[51] Int. Cl.[7] .................................................. A61M 37/00
[52] U.S. Cl. ............................. 604/95; 600/139; 600/146; 600/149
[58] Field of Search ............................... 604/95; 600/139, 600/146, 147, 149

[56] References Cited

U.S. PATENT DOCUMENTS

| | | | |
|---|---|---|---|
| 5,203,772 | 4/1993 | Hammerslag et al. | 604/95 |
| 5,318,526 | 6/1994 | Cohen | 604/95 |
| 5,381,782 | 1/1995 | DeLaRama et al. | 604/95 X |
| 5,396,880 | 3/1995 | Kagan et al. | 128/6 |
| 5,437,636 | 8/1995 | Snoke et al. | 604/95 |
| 5,454,787 | 10/1995 | Lundquist | 604/95 |
| 5,454,794 | 10/1995 | Narciso | 604/280 |
| 5,456,664 | 10/1995 | Heinzelman | 604/95 |
| 5,676,653 | 10/1997 | Taylor et al. | 604/95 |

*Primary Examiner*—Wynn Wood Coggins
*Assistant Examiner*—Cris L. Rodriguez

[57] ABSTRACT

A steerable catheter (310) having a handle, a manifold strain relief (314) securely mounted at a front distal end of the handle, a steering dial (316) rotatably mounted within the handle, the steering dial (316) comprises a steering dial left fastener (316L) and a steering dial right fastener (316R). A lumen extrusion shaft (318) is securely fastened at a rear distal end to the manifold strain relief(314). The lumen extrusion shaft (318) has at least one lumen extrusion shaft large lumen opening (318B) and at least one lumen extrusion shaft small lumen opening (318C) contained therein. A lumen extrusion tip (320) is securely fastened at a front distal end of the lumen extrusion shaft (318) by a lumen extrusion shaft connection (318A). A manifold (334) is securely fastened at a rear end of the manifold strain relief (314). At least one luer lock (324) is securely mounted at a rear distal end of the handle. A steering wire (328) securely fastened at a rear distal end to the steering dial (316). The steering wire (328) is slidably mounted within the manifold (334) and the manifold strain relief (314) and the lumen extrusion shaft (318). The steering wire (328) has a left steering wire (328L) securely fastened at a rear distal end to the steering dial left fastener (316L) and a right steering wire (328R) securely fastened at a rear distal end to the steering dial right fastener (316R). The steering wire (328) is slidably positioned within the at least one lumen extrusion shaft small lumen opening (318C). The steering wire (328) is securely affixed at a front end to the lumen extrusion shaft (318) by a lumen extrusion shaft small lumen attachment (318CA). The steering wire (328) terminates at a front distal end wire flat lumen extrusion tip which is securely mounted within the lumen extrusion tip (320). A catheter body lumen tubing (330) securely fastened at a rear distal end to the least one luer lock (324) and is securely fastened at a front distal end to the at least one lumen extrusion shaft large lumen opening (318B). A front end of the catheter body lumen tubing (330) is securely mounted within the manifold (334).

18 Claims, 8 Drawing Sheets

Fig. 2B

STEERABLE CATHETER

FIELD OF THE INVENTION

The present invention relates to a steerable catheter. More particularly, the present invention relates to a steerable catheter having an internal mechanism to enable a user to steer it left or right.

BACKGROUND OF THE INVENTION

Physicians utilize catheters in many procedures to gain access to interior remote regions of the body. It is a paramount factor that the physician has total control utilizing precise movements of the catheter when inside the body. Many of the invasive procedures within the body include entry into the heart especially when an ablation therapy is utilized. Thus, total and precise control over the tip of the catheter is required. In addition, it is preferable to have the physician control both the catheter as well as any device for treatment or observing when utilized within the body.

Numerous innovations for steerable catheters have been provided in the prior art that are described as follows. Even though these innovations may be suitable for the specific individual purposes to which they address, they differ from the present invention as hereinafter contrasted.

In U.S. Pat. No. 5,456,664, titled Catheter Steering Mechanism for pulling a first catheter steering wire while simultaneously allowing a second catheter steering wire to remain static, and vice versa. The mechanism includes at least one rotatable gear and means, such as a rotatable knob, for manually rotating the gear. A first linearly slidable toothed rack is attached to the proximal end of one steering wire, and a second linearly slidable toothed rack is attached to the proximal end of the other steering wire. A toothed gear rotatable by rotation of the knob engages each of the toothed racks to move them linearly in opposite directions in response to rotation of said gear. Preferably three intermeshing gears are used so that movement of the racks are in the same direction as the rotation of the knob. Preferably the steering wires are connected to the racks by connection that transfer tension as the racks move away from the wires but allow the wires to remain static, when the rack moves toward its associated wire.

In U.S. Pat. No. 5,454,794, titled Steerable Light Diffusing Catheter, invented by Hugh L. Narcisco, Jr. and Steven C. Anderson, titled Steerable Light Diffusing Catheter, a steerable catheter is disclosed which can treat luminal surfaces such as those occurring in the vascular tree, pulmonary tree, gastrointestinal tract, urological organs, etc. with Photodynamic Therapy (PDT) or other optical diffusing treatments. The catheter, which may include an inflatable balloon portion, has a light diffusing tip which can be deflected allowing the catheter to be steered precisely. The light diffusing tip on the steerable catheter is able to gain access to and enter virtually any sub-branch of the luminal system being treated. Since this catheter does not require a guidewire lumen for insertion, the profile is reduced. A low profile device allows treatment light to be delivered to the walls of the most distal, small diameter lumen.

In U.S. Pat. No. 5,437,636, titled Steerable Catheter with Fiberoptic Scope Inserting Means, invented by Phillip J. Snoke, David S. Rowley, David G. Lincoln and Kirk W. Charles, a catheter for use in body vessels or cavities has a housing of such size as to be readily held in the hand of a user and elongate tube means having one end connected to the housing and extending outwardly therefrom and being formed of material of such a stiffness so as to maintain the elongate tube means in straight condition in the absence of an external force applied thereto, where an outer end portion of the elongate tube means is flexible. Guide wires are connected to the housing by the inner ends thereof and extend outwardly therefrom through the elongate tube means. The outer ends of the guide wires are connected to the flexible outer end portion of the elongate tube means. Guide wire control means is carried by the housing and cooperates with the inner end portion of the guide wires for controlling the angular attitude of the flexible outer end portion of the elongate tube means.

In U.S. Pat. No. 5,396,880, titled Endoscope for Direct Visualization of the Spine and Epidural Space, invented by Jonathan Kagan, Roger White and David L. Brumfield, a system for direct visualization of the spine and the epidural and/or intra-discal space to facilitate diagnosis and treatment of spinal conditions is disclosure, which is adapted for percutaneous introduction into the spinal space. The system includes a disposable flexible catheter, a fiberoptic bundle disposed within the catheter which is connected to a light source and camera. The bundle is removably and adjustably connected to the proximal end of the catheter to permit rotation of the bundle relative to the catheter. A mechanism for controllably deflecting the tip of the catheter is provided to vary the viewing angle of the fiber-optic bundle within and to assist in steering the catheter through the spinal space. The mechanism includes a deflection wire extending through the catheter and affixed at the distal end thereof. The proximal end of the deflection wire is affixed to a sleeve which is slidably disposed around the catheter and within a housing. The housing includes an internal flange that defines a stop surface which is contacted by the sleeve as the catheter and deflection wire is moved in a first direction. After the sleeve contacts the stop surface, further movement of the catheter in the first direction causes tension in the wire between the sleeve and the wire's securement to the catheter, thereby bending the catheter tip in the direction of the securement. The catheter can be rotated with the tip in its deflected position to provide a conical viewing region within the spinal space.

The above described patented inventions differ from the present invention because they lack one or more of the following features described and claimed in the present invention: manifold strain relief, steering dial, lumen extrusion shaft having an upper lumen extrusion shaft large lumen opening and a lower lumen extrusion shaft large lumen opening and a pair of lumen extrusion shaft small lumen openings, lumen extrusion tip, fastening means, luer lock, steering wire, catheter body lumen tubing, steering wire guide, manifold, and/or hemostatis valve/touhy borst side port.

Numerous innovations for steerable catheters have been provided in the prior art that are adapted to be used. Even though these innovations may be suitable for the specific individual purposes to which they address, they would not be suitable for the purposes of the present invention as heretofore described.

SUMMARY OF THE INVENTION

The steerable catheter was developed to satisfy a need that every pain practitioner has faced for the last 60 years. The need to directly visualize the pathology in-situ in and around the nerve roots as they make their way out of neural foramina along the axis of the spinal cord. Other means of visualizations such as Fluoroscopy, MRI, and CAT Scans cannot produce real time images of the pathology or disease and cannot clearly differentiate soft tissue pathology. Epidural endoscopy was practically impossible if performed utilizing ridged optics and the paramedian or lumbar approach. This is due to the fact that the spinal cord is encased by an articulating bone structure with minimal access possibilities. Any device with the capability to access the epidural space would have to be flexible and very small. Using miniature fiberoptic endoscopes and miniature multi lumen steerable catheters the inventor has developed a medical device that introduces epidural space. The present invention allows physicians to directly visualize the epidural space of the spine and treat patients for related diseased in a minimally invasive manner.

A steerable catheter according to this invention is a video guided catheter having a four lumen catheter that incorporates the ability to steer the tip from left to right in one plane. The catheter consists of a body with integral steering mechanism and ports to access catheter lumens. The 0.100 inch diameter steerable catheter protrudes from the catheter body via a manifold that bifurcates the extruded catheter tubing into its four lumen components; two 0.014 inch diameter lumens for the steering wires, one 0.040 inch diameter lumen to pass the scope through the catheter, and one 0.040 inch diameter lumen for infusing fluids in the epidural space and passing instruments.

The present invention also can optionally utilize a kit consisting of disposable products that are used by the physician to access the epidural space through the sacral hiatus (tail bone). The kit contains drapes, syringe, needles, introducer set, etc.

The video system consists of a CCD camera, light source, and video monitor. The CCD camera is used to pickup the optical image from the endocoupler and convert it to an electronic signal that is sent to the video monitor. The light source consists of a bright light that is focused on the light fiber bundle to transmit light to the distal end of the scope.

The steerable catheter hereof consists of a plastic body (handle), four lumen PeBax (plastic) extruded catheter shaft tubing, a system to bifurcate the four lumen catheter shaft to points of origin within the housing, a mechanism to steer the catheter from left to right in one plane.

The plastic body (handle) consists of upper and lower halves that are injection molded and mate together at the central plane of the catheter body.

The catheter shaft is a four lumen extrusion with two larger 0.040 diameter holes and two smaller 0.014 diameter holes. The 0.040 diameter lumens are used to pass the Fiberscope and surgical instruments. The two 0.014 diameter lumens are used for passing the steering wires which are seated (fixed in place) at the catheter tip. The shaft is comprised of two different durometers of PeBax (plastic) tubing. The stiffer durometer is used for the 11 inch shaft and the softer durometer is used for the 1 inch tip. The function of the dual durometers for the catheter shaft is to provide a flexible top to allow for steering deflection and a stiff shaft that allows the catheter to be advanced during the procedure without buckling.

The four lumen extruded tubing is bifurcated by a manifold located at the front of the handle assembly. From the bifurcation point the 0.040 diameter holes are ported to the rear of the catheter body via tubing which mates to standard Touhy Borst valves. At the point of bifurcation the steering wires enter the catheter shaft.

The mechanism used to steer the catheter consists of a steering dial that is trapped between the upper and lower handle in assembly and is allowed to rotate on its axis. The steering dial incorporates posts located 180 degrees apart to which the steering wires are anchored. The steering wire runs from the respective post through the point of bifurcation (at the manifold) and up the catheter shaft where it is anchored at the tip of the catheter shaft. When the steering dial is rotated it displaces the steering wires attached to the posts by means of rotational translation. This puts one wire in tension and one wire in compression. This force is transferred through the wire to the tip of the catheter causing the tip to deflect in the direction of rotation of the steering dial. Oscillating the dial from left to right causes the tip of the catheter to steer from left to right in one plane. The catheter is rotated 90 degrees to steer the catheter in a plane at right angles to the current steering plane.

There are currently other types of steerable catheters on the market. Due to the miniaturized size of the present invention, the inventor was forced to develop a new and improved steering system. Through trial and error the inventor made several different wire configurations for the steering system. The configuration of the steering wires in relation to how they are formed and anchored in the tip of the catheter is a unique feature to the present invention.

The endocoupler used in conjunction with the video guided catheter is a Fiberscope that is inserted through one of the 0.040 diameter channels in the catheter and allows the physician to view images through the end of the catheter, hence "video guided catheter". The fiberoptic endoscope relays the optical image to the endocoupler. The fiberoptic endoscope consists of an image fiber bundle and a light fiber bundle. The image fiber bundle is comprised of extremely small glass fibers (10,000 individual fibers in a ½ mm bundle) that are drawn in a coherent manner as to relay the image from the distal end of the scope to the image fiber coupler where the endoscope connects to the endocoupler. A small lens is mounted at the distal end of the scope to relay and focus the image to the fiberoptic image bundle. The light bundle is used to provide illumination at the distal end of scope for viewing. Both the image fiber bundle and the light fiber bundle are encased in flexible tubing and run parallel for the length of the scope. The two fiber bundles bifurcate at the image fiber coupler (body of the scope) where the image fiber terminates and the light fiber bundle passes to the light source. The image fiber coupler in turn is connected to the endocoupler. A collet assembly is used to make the connection between the endocoupler and the image fiber coupler of the fiberoptic endoscope.

The types of problems encountered in the prior art are steerable catheter have too large a lumen extrusion tip and lumen extrusion shaft to be utilized in small spaces. In addition, the steering mechanism of the prior art is not precise enough to navigate through complex confined matrices within the body.

In the prior art, unsuccessful attempts to solve this problem were attempted namely: steerable catheters having rotational dials. However, the problem was solved by the present invention because the steering dial works in unison with the steering wires in conjunction with the catheter body lumen tubing, which in turn operates in conjunction with the soft lumen extrusion tip and hard lumen extrusion shaft.

Innovations within the prior art are rapidly being exploited in the field of steerable catheters.

The present invention went contrary to the teaching of the art which teaches steerable catheters having dials which do not work in unison with the steering wires in conjunction with the catheter body lumen tubing in conjunction with the soft lumen extrusion tip and hard lumen extrusion shaft.

The present invention solved a long felt need for a small steerable catheter with extremely precise ability for an user to control movement of the lumen extrusion tip.

The present invention produced unexpected results namely: the lumen extrusion tip not only has very precise control but the user can actually separate tissue as well as other objects due to inherent strength therein.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawings.

DESCRIPTION OF THE PREFERRED EMBODIMENT

Figure 1A:
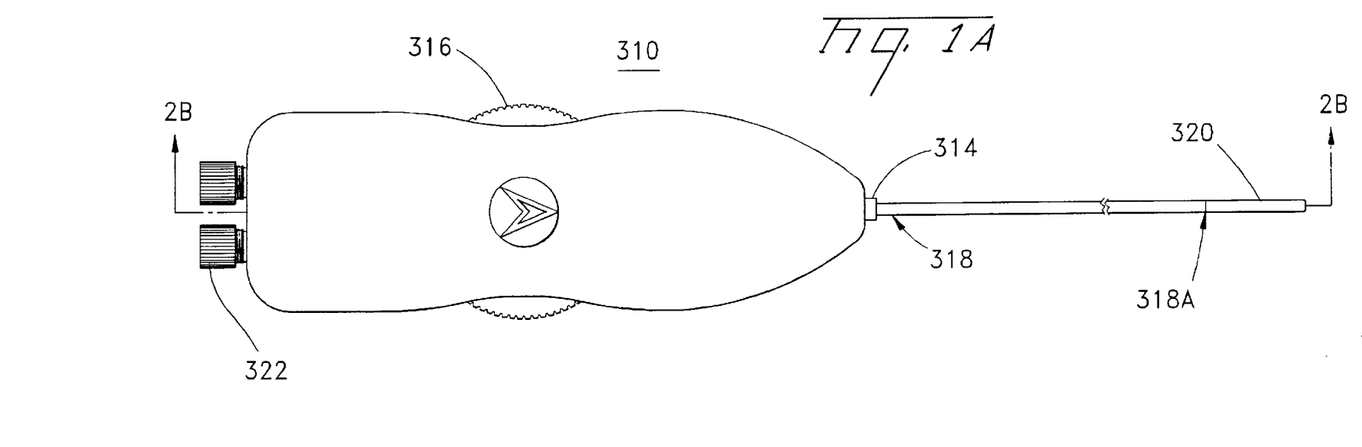
FIG. 1A is a top view of a steerable catheter in accordance with the present invention.
Figure 1B:
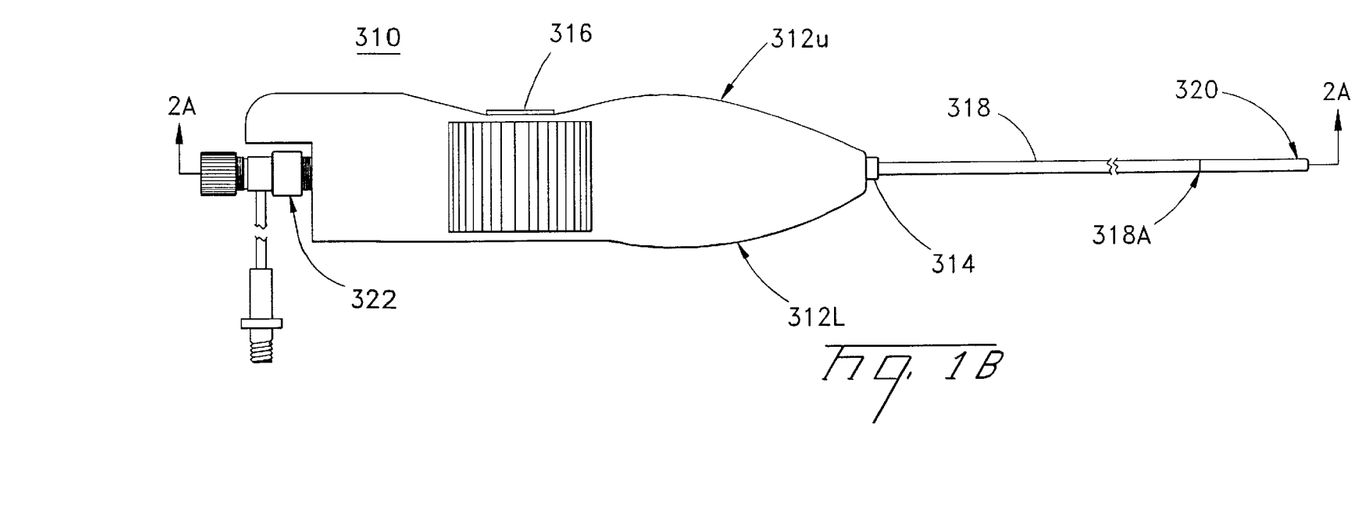
FIG. 1B is a side view of the steerable catheter hereof.

Firstly, referring to FIG. 1A which is a top view of a steerable catheter (310) and FIG. 1B which is a side view of a steerable catheter (310), there is shown a steerable catheter (310) comprising a handle having a steering dial (316) rotatably mounted therein. The handle comprises an upper handle (312U) securely attached to a lower handle (312L) by upper handle crash pins (326U) and lower handle crash pins (326L), respectively. The upper handle crash pins (326U) are used to guide and align upper handle (312U) and lower handle (312L) in assembled female portion. The lower handle crash pins (326L) are used to guide and align upper and lower handle in assembled male portion. The lower handle (312L) is preferably ABS injection molded and designed to locate steering dial (316) and luer lock (324). The upper handle (312U) is preferably injection molded and is designed to locate steering dial (316), luer locks (324) and manifold (334). The handle is manufactured from a material selected from a group consisting of plastic, plastic composite, metal, metal alloy, fiberglass, epoxy, carbon-graphite, ceramic, wood, wood composite, rubber, and rubber composite. The handle is preferably manufactured from plastic or plastic composite material.

Figure 2A:
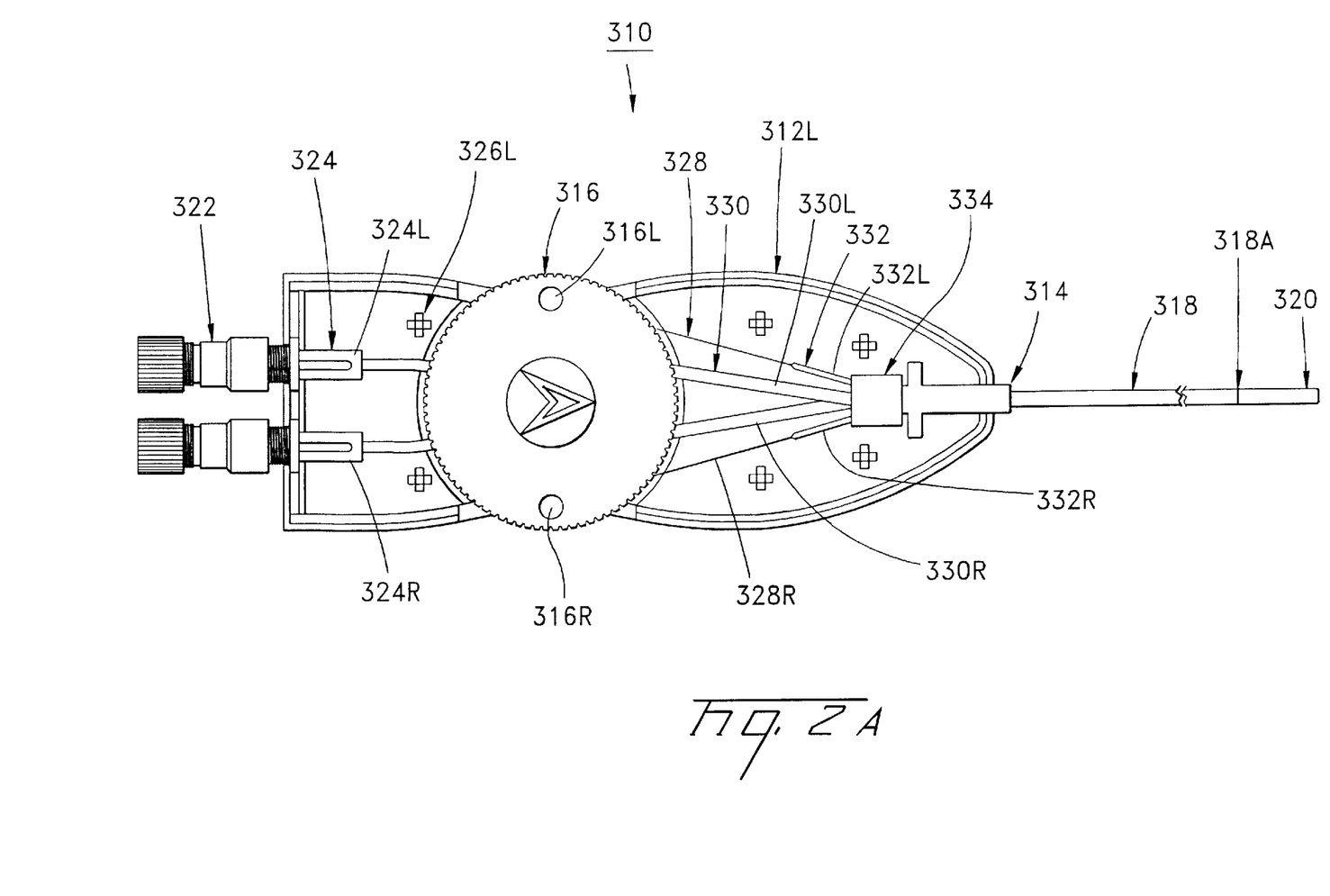
FIG. 2A is a cross-sectional top view of the steerable catheter hereof, taken along line 2A—2A of FIG. 1B.
Figure 2B:
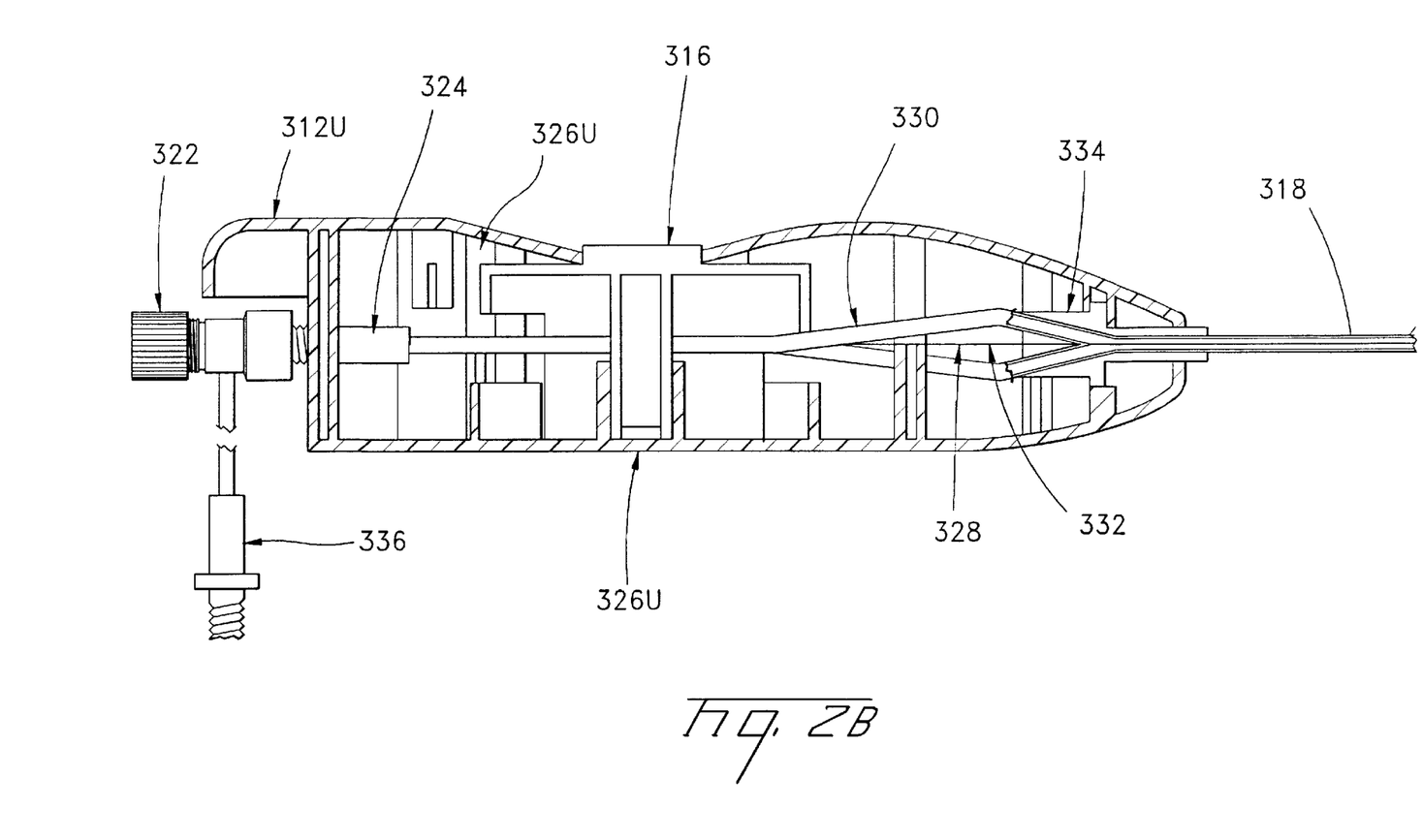
FIG. 2B is a cross-sectional top view of the steerable catheter hereof, taken along line 2B—2B of FIG. 1A.

Referring to FIG. 2A, which is a cross-sectional top view of a steerable catheter (310) taken along line 2A—2A of FIG. 1B, and FIG. 2B, which is a cross-sectional top view of a steerable catheter (310) taken along line 2B—2B of FIG. 1A, there is shown steerable catheter (310) comprising a handle. The steerable catheter (310) further comprises a manifold strain relief (314) securely mounted at a front distal end of the handle.

The steerable catheter (310) further comprises a steering dial (316) rotatably mounted within the handle. The steering dial (316) comprises a steering dial left fastener (316L) and a steering dial right fastener (316R). The steering dial (316) is used by the operator to steer the lumen extrusion tip (320) back and forth in one plane. The lumen extrusion tip (320) is preferably manufactured from a softer durometer 4033 PeBax four lumen extrusion where wire (320AA, 320BA, 320CA, 320DA) is seated at lumen extrusion tip (320) by melting (tipping) plastic around the wire (320AA, 320BA, 320CA, 320DA) in the first 0.15 to 0.20 inches of tip. The steering dial (316) has molded posts with slots which are the steering dial left fastener (316L) and the steering dial right fastener (316R) that function to connect the left steering wire (328L) and the right steering wire (328R) to the steering dial (316).

The steerable catheter (310) further comprises a lumen extrusion shaft (318) securely fastened at a rear distal end to the manifold strain relief (314). The lumen extrusion shaft (318) comprises at least one lumen extrusion shaft large lumen opening (318B) and at least one lumen extrusion shaft small lumen opening (318C) contained therein, see FIG. 3C.

The steerable catheter (310) further comprises a lumen extrusion tip (320) securely fastened at a front distal end of the lumen extrusion shaft (318) by a lumen extrusion shaft connection (318A). The lumen extrusion shaft connection (318A) is a fusion joint where a softer durometer tip is fused to a harder durometer shaft. The lumen extrusion tip (320) is selected from a group consisting of looped wire lumen extrusion tip (320A), continuous looped wire lumen extrusion tip (320B), formed hook wire lumen extrusion tip (320C), ballized wire lumen extrusion tip (320D), and plastic wire lumen extrusion tip (320E).

The steerable catheter (310) further comprises a manifold (334) securely fastened at a rear end of the manifold strain relief (314). The manifold (334) is a bifurcation point where transition is made between integral four lumen extrusion to individual tubes. The manifold strain relief (314) portion of manifold (334) extends beyond the handle (312U, 312L) assembly.

The steerable catheter (310) further comprises at least one luer lock (324) securely mounted at a rear distal end of the handle. The luer lock (324) is a transition coupling between catheter body lumen tubing (330) and hemostatis valve/ touhy borst side port (336). Wings and flanges on luer lock (324) sit in slots that are molded into the upper handle (312U) and the lower handle (312L) to capture the luer lock and hold the hemostatis valve/touhy borst side port (336) in place.

The luer lock (324) comprises a fastening means (322) removably attached to a rear end thereof. The fastening means (322) is further connected to a hemostatis valve/touhy borst side port (336). The hemostatis valve/touhy borst side port (336) is used to pass and seal around scopes and instruments inserted through the steerable catheter. The side port is used to infuse saline to distend the epidural space and pass other fluids through the steerable catheter lumen. The hemostatis valve/touhy borst side port (336) are used to pass and seal around scopes and instruments inserted through the steerable catheter (310).

The steerable catheter (310) further comprises a steering wire (328) securely fastened at a rear distal end to the steering dial (316). The steering wire (328) is slidably mounted within the manifold (334) and the manifold strain relief (314) and the lumen extrusion shaft (318). The lumen extrusion shaft (318) is preferably manufactured from a harder durometer 7033 PeBax four lumen extrusion tubing. The steering wire (328) comprises a left steering wire (328L) securely fastened at a rear distal end to the steering dial left fastener (316L) and a right steering wire (328R) securely fastened at a rear distal end to the steering dial right fastener (316R). The steering wire (328) is slidably positioned within the at least one lumen extrusion shaft small lumen opening (318C). The steering wire (328) is securely affixed at a front end to the lumen extrusion shaft (318) by a lumen extrusion shaft small lumen attachment (318CA). The steering wire (328) terminates at a front distal end wire lumen extrusion tip which is securely mounted within the lumen extrusion tip (320). The steering wire guide (332) is preferably composed of a left steering wire guide (332L) and a right steering wire guide (332R). The left steering wire guide (332L) and the right steering wire guide (332R) are tubing used to pass the left steering wire (328L) and the right steering wire (328R), respectively, from lumen extrusion shaft (318) into catheter body via the manifold (334). The left steering wire (328L) is slidably positioned within a left steering wire guide (332L) which is securely attached to a rear end of the manifold (334) and the right steering wire (328R) is slidably positioned within right steering wire guide (332R) which is securely attached to a rear end of the manifold (334). The steering wire (328) is seated in lumen extrusion tip (320) and passes through extruded lumen extrusion shaft small lumen opening (318C) which are wire channels where they exit from the manifold (334) and run to the steering dial (316).

The steerable catheter (310) further comprises a catheter body lumen tubing (330) securely fastened at a rear distal end to the least one luer lock (324) and securely fastened at a front distal end to the at least one lumen extrusion shaft large lumen opening (318B). A front end of the catheter body lumen tubing (330) is securely mounted within the manifold (334). The catheter body lumen tubing (330) comprises a left catheter body lumen tubing (330L) securely attached at a rear distal end to a left luer lock (324L) and attached at a front distal end to an upper lumen extrusion shaft large lumen opening (318BU) within the manifold (334). The catheter body lumen tubing (330) further comprises a right catheter body lumen tubing (330R) securely attached at a rear distal end to a right luer lock (324R) and attached at a front distal end to a lower lumen extrusion shaft large lumen opening (318BL) within the manifold (334). The catheter body lumen tubing (330) connects the four lumen extrusion scope and working channel lumens which are lumen extrusion shaft large lumen openings (318B) to the respective luer lock (324) via bifurcation point in the manifold (334).

Figures 3A, 3B, 3C, 3D:
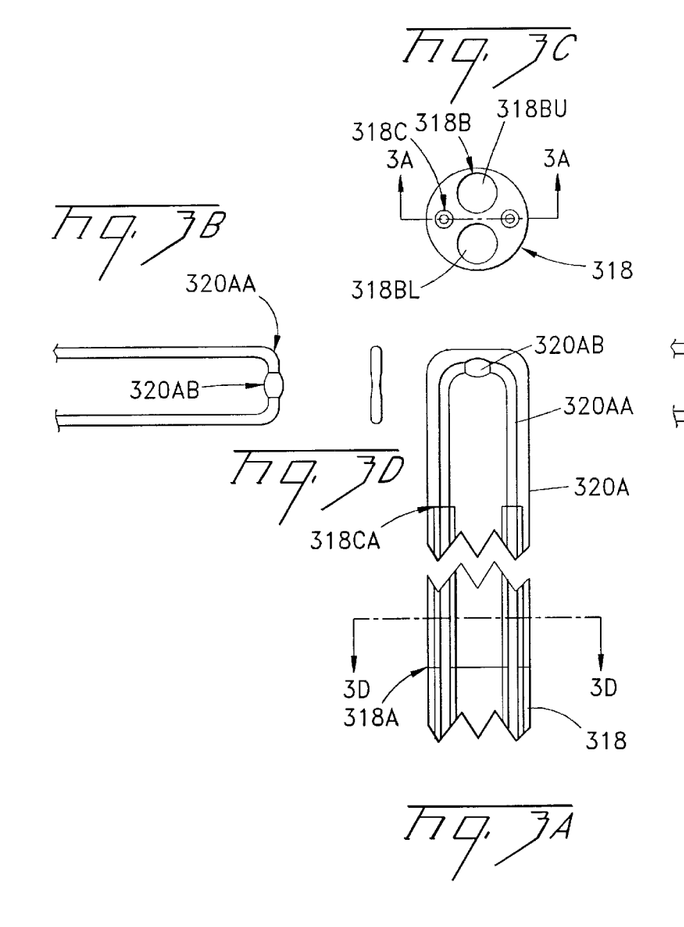
FIG. 3A is a longitudinal cross-sectional view of a looped wire lumen extrusion tip taken along line 3A—3A of FIG. 3C.
FIG. 3B is a top view of a looped wire exhibiting a looped wire radius securely affixed at a front middle distal end thereof.
FIG. 3C is a cross-sectional view of a looped wire lumen extrusion tip forming a part of this invention.
FIG. 3D is a cross-sectional view of a looped wire taken along line 3E—3E of FIG. 3B exhibiting a looped wire radius securely affixed at a front middle distal end thereof.

Referring to FIG. 3A, which is a longitudinal cross-sectional view of a looped wire lumen extrusion tip (320A) taken along line 3A—3A of FIG. 3C and FIG. 3C, which is a cross-sectional view of a looped wire lumen extrusion tip (320A), there is shown a looped wire lumen extrusion tip (320A) which is the preferred embodiment as used in the steerable catheter (310). This approach uses a continuous stainless steel steering wire that runs up one lumen extrusion shaft small lumen opening (318C) of the lumen extrusion tip (320), is bent 180 degrees, and runs back down the other lumen extrusion shaft small lumen opening (318C) of the lumen extrusion shaft (318). The distal end of the lumen extrusion tip (320) is heated to melt the plastic surrounding the looped wire (320AA) which seats the looped wire (320AA) therein.

Referring to FIG. 3B which is a top view of a looped wire (320AA), there is shown a looped wire radius (320AB) securely affixed at a front middle distal end thereof. FIG. 3D which is a cross-sectional view of a looped wire (320AA) taken along line 3E—3E of FIG. 3B, there is further shown the looped wire radius (320AB) securely affixed at a front middle distal end thereof. The design employs a looped wire (320AA) with a looped wire radius (320AB) that is formed in the center of the lumen extrusion tip (320). This allows a 0.010" diameter looped wire (320AA) to pass between the 0.005" wall thickness of the two lumen extrusion shaft large lumen openings (318B). The looped wire radius (320AB) is formed by coining the center of the looped wire (320AA) bend between two 0.040" diameter rods on a forming tool.

Figures 4A, 4B, 4C:
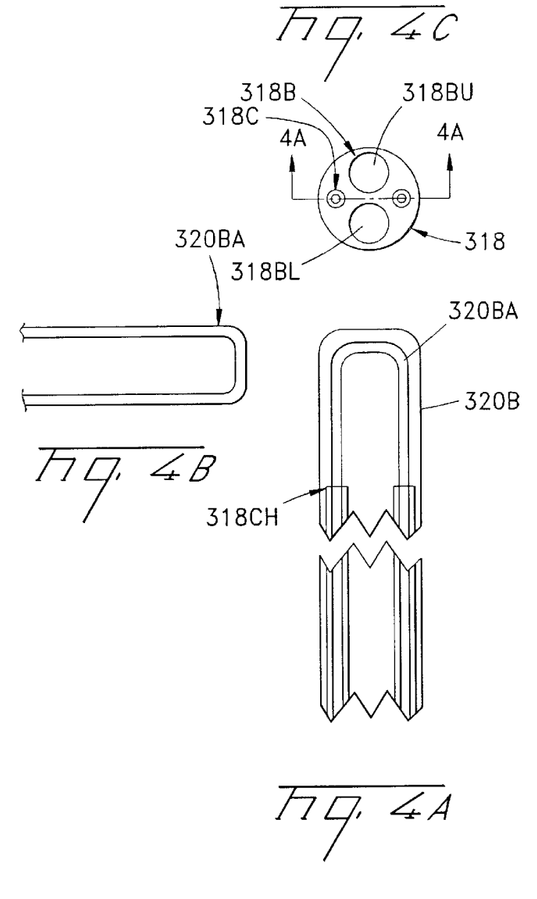
FIG. 4A is a longitudinal cross-sectional view of a continuous looped wire lumen extrusion tip taken along line 4A—4A of FIG. 4C.
FIG. 4B is a top view of a continuous looped wire.
FIG. 4C is a cross-sectional view of a continuous looped wire lumen extrusion tip.

Referring to FIG. 4A which is a longitudinal cross-sectional view of a continuous looped wire lumen extrusion tip (320B) taken along line 4A—4A of FIG. 4C, FIG. 4B which is a top view of a continuous looped wire (320BA), and FIG. 4C which is a cross-sectional view of a continuous looped wire lumen extrusion tip (320B) it will be observed that the continuous looped wire lumen extrusion tip (320B) uses a continuous stainless steel steering continuous looped wire (320BA) that runs up one lumen extrusion shaft small lumen opening (318C) of the lumen extrusion tip (320), is bent 180 degrees, and runs back down the other lumen extrusion shaft small lumen opening (318C) of the catheter body lumen tubing (330). The design employs 0.005" diameter wire to pass between the 0.005" wall thickness of the two lumen extrusion shaft large lumen openings (318B). The distal end of the lumen extrusion tip (320) is heated to melt the plastic surrounding the continuous looped wire (320BA) which seats the continuous looped wire (320BA) therein.

Figure 5A:
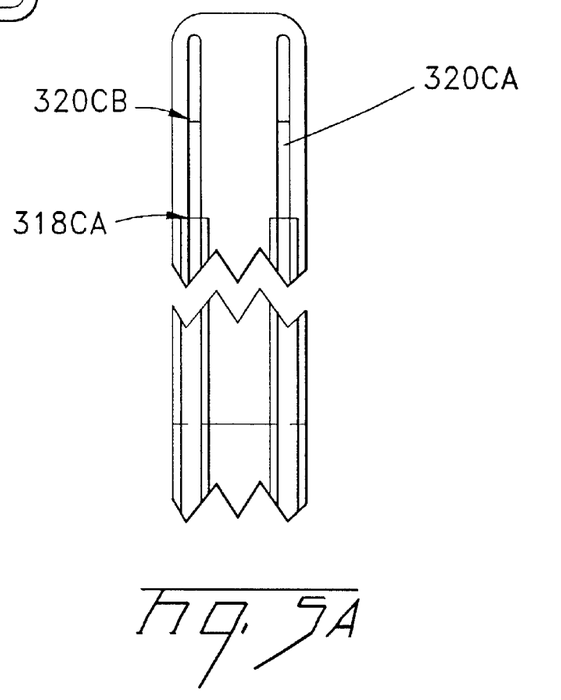
FIG. 5A is a longitudinal cross-sectional view of a formed hook wire lumen extrusion tip taken along line 5A—5A of FIG. 5C.
Figure 5B:
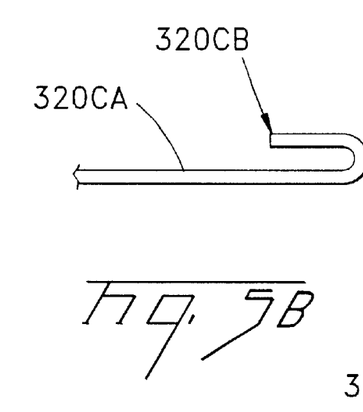
FIG. 5B is a top view of a formed hook wire exhibiting a formed hook wire hook at a front distal end thereof.
Figure 5C:
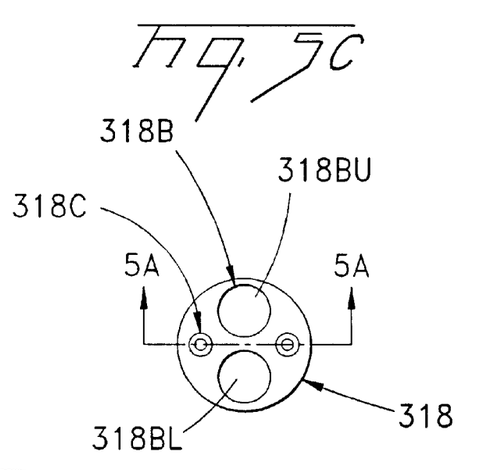
FIG. 5C is a cross-sectional view of a formed hook wire lumen extrusion tip.

Referring to FIG. 5A, which is a longitudinal cross-sectional view of a formed hook wire lumen extrusion tip (320C), taken along line 5A—5A of FIG. 5C, FIG. 5B, which is a top view of a formed hook wire (320CA) exhibiting a formed hook wire hook (320CB) at a front distal end thereof, and FIG. 5C which is a cross-sectional view of a formed hook wire lumen extrusion tip (320C), the formed hook wire lumen extrusion tip (320C) uses two separate stainless steel steering formed hook wire (320CA) that runs up the lumen extrusion shaft small lumen opening (318C) of the four lumen extrusion catheter body lumen tubing (330). The design employs two 0.010" diameter formed hook wires (320CA) with small formed bends on the end to create a "formed wire hook (320CB)". The distal end of the lumen extrusion tip (320) is heated to melt the plastic surrounding the continuous formed hook wires (320CA) and respective formed hook wire hooks (320CB) which seats them therein.

Figures 6A, 6B, 6C, 7A, 7B, 7C:
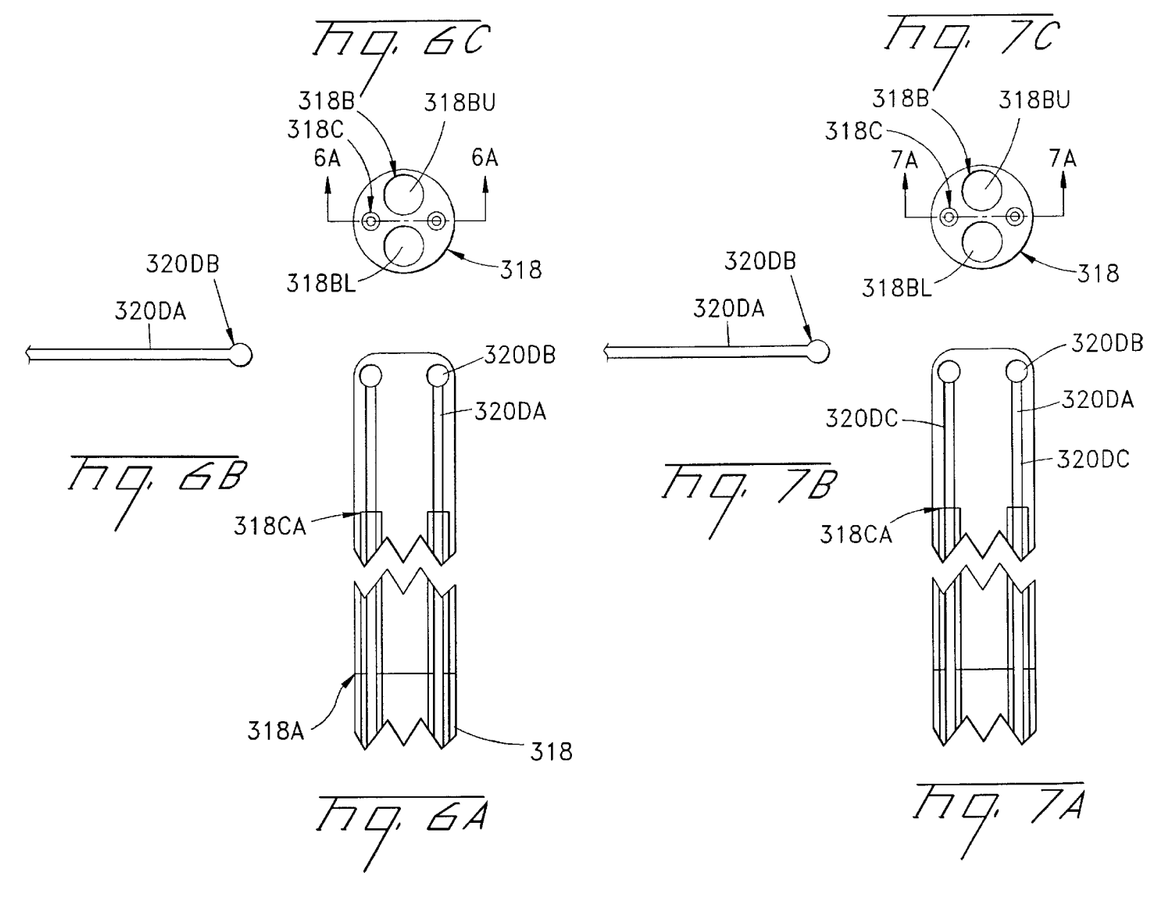
FIG. 6A is a longitudinal cross-sectional view of a ballized wire lumen extrusion tip taken along line 6A—6A of FIG. 6C.
FIG. 6B is a top view of a ballized wire exhibiting a ballized wire steel ball securely affixed at a front distal end thereof.
FIG. 6C is a cross-sectional view of a ballized wire lumen extrusion tip.
FIG. 7A is a longitudinal cross-sectional view of a ballized wire lumen extrusion tip taken along line 7A—7A of FIG. 7C.
FIG. 7B is a top view of a ballized wire exhibiting a ballized wire steel ball securely affixed at a front distal end thereof and a ballized wire jacket securely positioned around the ballized wire.
FIG. 7C is a cross-sectional view of a ballized wire lumen extrusion tip.

Referring to FIG. 6A, which is a longitudinal cross-sectional view of a ballized wire lumen extrusion tip (320D), taken along line 6A—6A of FIG. 6C, FIG. 6B, which is a top view of a ballized wire (320DA) exhibiting a ballized wire steel ball (320DB) securely affixed at a front distal end thereof, and FIG. 6C which is a cross-sectional view of a ballized wire lumen extrusion tip (320D), it will be noted that the ballized wire lumen extrusion tip (320D) uses two separate stainless steel ballized wires (320DA) that run up the lumen extrusion shaft small lumen openings (318C) of the four lumen extrusion catheter body lumen tubing (330). The design employs two 0.010" diameter ballized wires (320DA) with 0.020" diameter ballized wire steel balls (320DB) welded to the distal end of the ballized wires (320DA). The distal end of the lumen extrusion tip (320) is heated to melt the plastic surrounding the ballized wires (320DA) and respective ballized wire steel ball (320DB) which seats them therein.

Referring to FIG. 7A, which is a longitudinal cross-sectional view of a ballized wire lumen extrusion tip (320D), taken along line 7A—7A of FIG. 7C, FIG. 7B, which is a top view of a ballized wire (320DA) exhibiting a ballized wire steel ball (320DB) securely affixed at a front distal end thereof and a ballized wire jacket (320DC) securely positioned around the ballized wire (320DA), and FIG. 7C, which is a cross-sectional view of a ballized wire lumen extrusion tip (320D), show an embodiment of the ballized wire lumen extrusion tip (320D) using two separate stainless steel ballized wires (320DA) that run up the lumen extrusion shaft small lumen openings (318C) of the four lumen extrusion catheter body lumen tubing (330). The design employs two 0.010" diameter ballized wires (320DA) with 0.020" diameter ballized wire steel balls (320DB) welded to the distal end of the ballized wires (320DA). UV curable epoxy glue is injected into the lumen extrusion shaft small lumen openings (318C) prior to pulling the ballized wire steel balls (320DB) into the extrusion. The epoxy ballized wire jacket (320DC) is UV cured and the distal end of lumen extrusion tip (320) is heated to melt the plastic surrounding the ballized wires (320DA), respective ballized wire steel ball (320DB) and respective ballized wire jacket (320DC) which seats them therein.

Figures 8A, 8B, 8C, 9A, 9B, 9C:
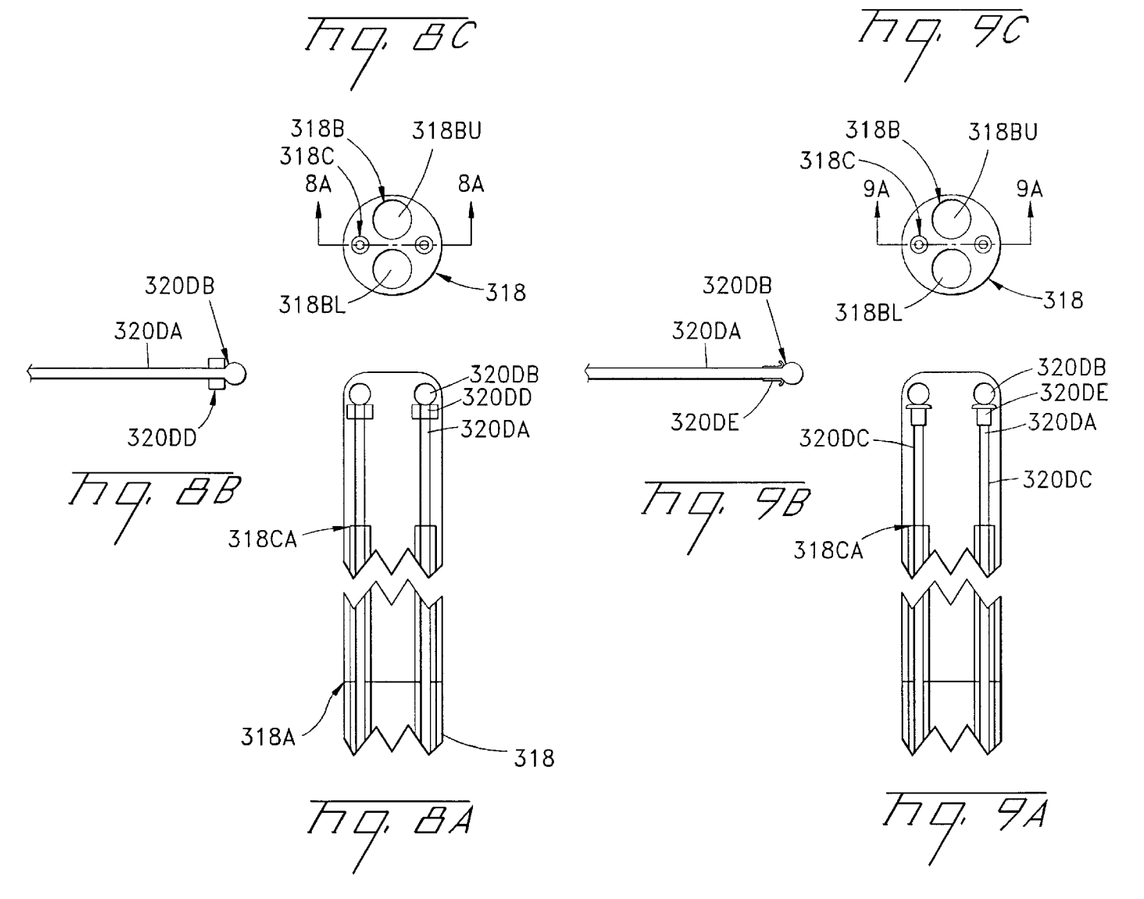
FIG. 8A is a longitudinal cross-sectional view of a ballized wire lumen extrusion tip taken along line 8A—8A of FIG. 8C.
FIG. 8B is a top view of a ballized wire exhibiting a ballized wire steel ball securely affixed at a front distal end thereof and a ballized wire washer securely positioned around the ballized wire adjacent to the ballized wire steel ball.
FIG. 8C is a cross-sectional view of a ballized wire lumen extrusion tip.
FIG. 9A is a longitudinal cross-sectional view of a ballized wire lumen extrusion tip taken along line 9A—9A of FIG. 9C.
FIG. 9B is a top view of a ballized wire exhibiting a ballized wire steel ball securely affixed at a front distal end thereof and a ballized wire eyelet securely positioned around the ballized wire adjacent to the ballized wire steel ball.
FIG. 9C is a cross-sectional view of a ballized wire lumen extrusion tip.
Figure 10A:
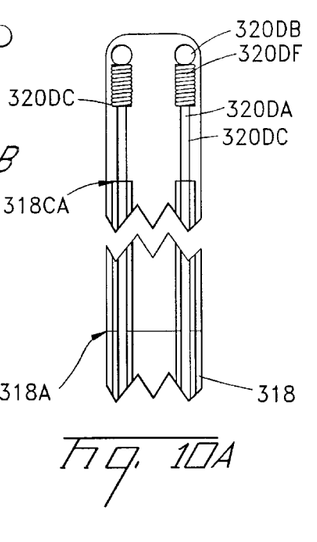
FIG. 10A is a longitudinal cross-sectional view of a ballized wire lumen extrusion tip taken along line 10A—10A of FIG. 10C.
Figure 10B:
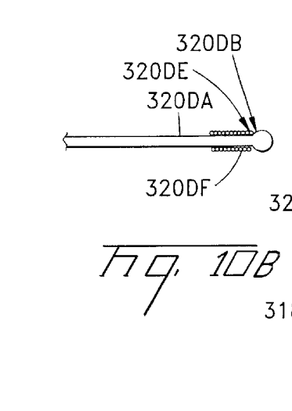
FIG. 10B is a top view of a ballized wire exhibiting a ballized wire steel ball securely affixed at a front distal end thereof and a ballized wire spring adjacent to the ballized wire steel ball.
Figure 10C:
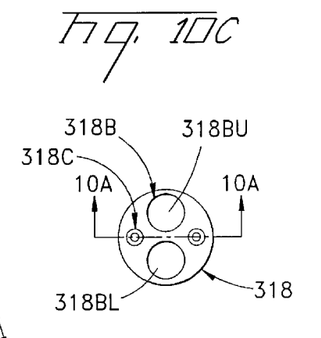
FIG. 10C is a cross-sectional view of a ballized wire lumen extrusion tip.
Figures 11A, 11B, 11C:
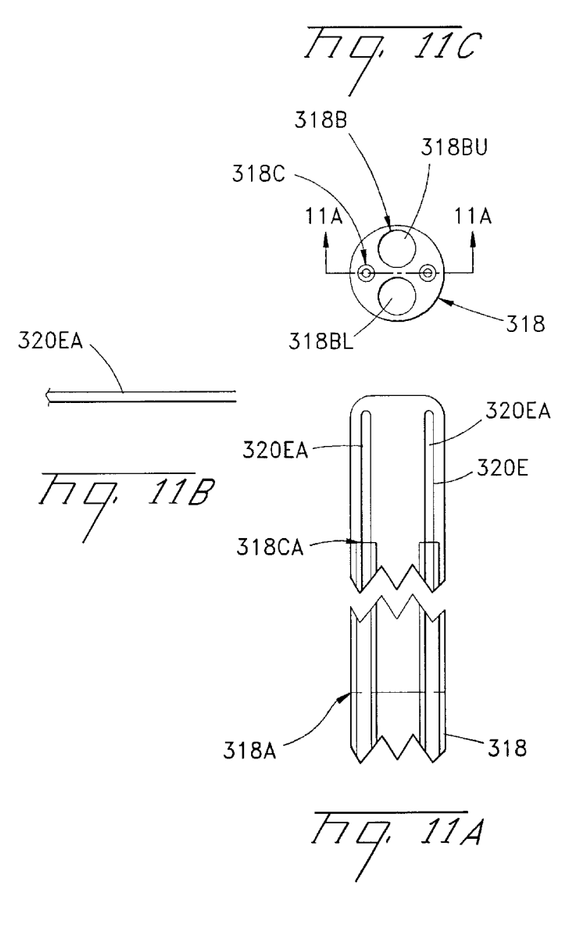
FIG. 11A is a longitudinal cross-sectional view of a plastic wire lumen extrusion tip taken along line 11A—11A of FIG. 11C exhibiting the plastic wire securely affixed therein by a thermo-bonding process.
FIG. 11B is a top view of a plastic wire.
FIG. 11C is a cross-sectional view of a plastic wire lumen extrusion tip.

Referring to FIG. 8A which is a longitudinal cross-sectional view of a ballized wire lumen extrusion tip (320D), taken along line 8A—8A of FIG. 8C, FIG. 8B, which is a top view of a ballized wire (320DA) exhibiting a ballized wire steel ball (320DB) securely affixed at a front distal end thereof and a ballized wire washer (320DD) securely positioned around the ballized wire (320DA) adjacent to the ballized wire steel ball (320DB), and FIG. 8C, which is a cross-sectional view of a ballized wire lumen extrusion tip (320D), there is shown a ballized wire lumen extrusion tip (320D) using two separate stainless steel ballized wires (320DA) that run up the lumen extrusion shaft small lumen openings (318C) of the four lumen extrusion catheter body lumen tubing (330). The design employs two 0.010" diameter ballized wires (320DA) with 0.020" diameter ballized wire steel balls (320DB) welded to the distal end of the ballized wires (320DA). A ballized wire washer (320DD) with a 0.024" outside diameter and a 0.012" inside diameter is slid over each of the ballized wires (320DA) and up to the ballized wire steel ball (320DB) and pulled into the lumen extrusion shaft small lumen openings (318C) of the lumen extrusion tip (320). The distal end of the lumen extrusion tip (320) is heated to melt the plastic surrounding the ballized wires (320DA), respective ballized wire steel ball (320DB), and respective ballized wire washer (320DD) which seats them therein Referring to FIG. 9A, which is a longitudinal cross-sectional view of a ballized wire lumen extrusion tip (320D), taken along line 9A—9A of FIG. 9C, FIG. 9B which is a top view of a ballized wire (320DA) exhibiting a ballized wire steel ball (320DB) securely affixed at a front distal end thereof and a ballized wire eyelet (320DE) securely positioned around the ballized wire (320DA) adjacent to the ballized wire steel ball (320DB), and FIG. 9C which is a cross-sectional view of a ballized wire lumen extrusion tip (320D), it will be noted that the ballized wire lumen extrusion tip (320D) uses two separate stainless steel ballized wires (320DA) that run up the lumen extrusion shaft small lumen openings (318C) of the four lumen extrusion catheter body lumen tubing (330). The design employs two 0.010"

diameter ballized wires (320DA) with 0.020" diameter ballized wire steel balls (320DB) welded to the distal end of the ballized wires (320DA). A stainless steel ballized wire eyelet (320DE) with a 0.024" outside diameter and a 0.012" inside diameter is slid over each of the ballized wires (320DA) and up to each of the ballized wire steel balls (320DB) and pulled into the lumen extrusion shaft small lumen openings (318C) of the lumen extrusion tip (320). The distal end of the lumen extrusion tip (320) is heated to melt the plastic surrounding the ballized wires (320DA), respective ballized wire steel ball (320DB), and respective ballized wire eyelet (320DE) which seats them therein Referring to FIG. 10A, which is a longitudinal cross-sectional view of a ballized wire lumen extrusion tip (320D), taken along line 10A—10A of FIG. 10C, FIG. 10B which is a top view of a ballized wire (320DA) exhibiting a ballized wire steel ball (320DB) securely affixed at a front distal end thereof and a ballized wire eyelet (320DE) securely positioned around the ballized wire spring (320DF) adjacent to the ballized wire steel ball (320DB), and FIG. 10C which is a cross-sectional view of a ballized wire lumen extrusion tip (320D), the ballized wire lumen extrusion tip (320D) uses two separate stainless steel ballized wires (320DA) that run up the lumen extrusion shaft small lumen openings (318C) of the four lumen extrusion catheter body lumen tubing (330). The design employs two 0.010" diameter ballized wires (320DA) with 0.020" diameter ballized wire steel balls (320DB) welded to the distal end of the ballized wires (320DA). A stainless steel ballized wire spring (320DF) with a 0.024" outside diameter and a 0.012" inside diameter is slid over each of the ballized wires (320DA) and up to each of the ballized wire steel balls (320DB) and pulled into the lumen extrusion shaft small lumen openings (318C) of the lumen extrusion tip (320). The distal end of the lumen extrusion tip (320) is heated to melt the plastic surrounding the ballized wires (320DA), respective ballized wire steel ball (320DB), and respective ballized wire spring (320DF) which seats them therein Finally, referring to FIG. 11A which is a longitudinal cross-sectional view of a plastic wire lumen extrusion tip (320E), taken along line 11A—11A of FIG. 11C exhibiting the plastic wire (320EA) securely affixed therein by a thermo-bonding process, FIG. 11B which is a top view of a plastic wire (320EA), and FIG. 11C, which is a cross-sectional view of a plastic wire lumen extrusion tip (320E), shows further embodiment using two separate steering plastic wires (320EA) that run up the lumen extrusion shaft small lumen openings (318C) of the four lumen extrusion catheter body lumen tubing (330). The design employs two 0.010" diameter plastic wires (320EA) that are pulled into the lumen extrusion shaft small lumen openings (318C) of the lumen extrusion tip (320). The distal end of the plastic wire lumen extrusion tip (320E) is heated to melt the plastic wires (320EA) into the surrounding plastic wire lumen extrusion tip (320E) which seats the plastic wires (320EA) therein.

It will be understood that each of the elements described above, or two or more together, may also find a useful application in other types of constructions differing from the type described above.

While the invention has been illustrated and described as embodied in a steerable catheter, it is not intended to be limited to the details shown, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

What is claimed is:

1. A steerable catheter assembly comprising:
    a.) a handle having first and second ends and containing a steering dial mounted for rotative movement therebetween, a manifold having a first pair of openings and a second pair of openings disposed at said first end, and a pair of first and second luer locks disposed at said second end;
    b.) a lumen extension shaft having a proximal and distal ends, said lumen extension shaft proximal end securely fastened to said handle first end in communication with said manifold, said shaft including a pair of first tubing members passing respectively through said first openings, and a second pair of tubing members passing respectively through said second openings, where said lumen extension shaft is made of a material having a first degree of rigidity;
    c.) a lumen extrusion tip having a proximal end securely fastened to the distal end of said lumen extension shaft, where said lumen extrusion tip is made of a material having less rigidity than said lumen extension shaft;
    d.) means accessible through said first and second luer locks for inserting an imagining instrument through said manifold and at least one of said first tubing members for remote viewing of the region around said lumen extrusion tip; and
    e.) a pair of steering wires securely fastened at first ends therof to first and second sides, respectively, of said steering dial, said steering wires being slidably mounted within said manifold, through said second openings and said second tubing members, and secured at a second end thereof to said lumen extrusion tip, whereby movement of said lumer extrusion tip to plural positions may be made within a fixed plane.

2. The steerable catheter assembly according to claim 1, wherein a strain relief member is provided adjacent said manifold, and through which said lumen extrusion shaft extends.

3. The steerable catheter assembly according to claim 1, wherein said lumen extrusion tip is an element selected from the group of a looped wire, a formed hook wire, a ballized wire, and a plastic wire.

4. The steerable catheter assembly according to claim 3, wherein said lumen extrusion tip is a looped wire comprising a looped wire having a reverse bend radius.

5. The steerable catheter assembly according to claim 4, wherein said looped wire comprises a 0.010" diameter wire formed by coining a center of the looped wire between two 0.040" diameter rods on a forming tool where the looped wire includes an end heated to weld and form the loop.

6. The steerable catheter assembly according to claim 3, wherein said lumen extrusion tip is a continuous looped wire.

7. The steerable catheter assembly according to claim 4, wherein said lumen extrusion tip is a formed hook wire comprising a pair of wires, each having a formed hook at a front distal end.

8. The steerable catheter assembly according to claim 3, wherein said lumen extrusion tip is a ballized wire comprising a pair of wires, each terminating at a steel ball, where the diameter of each said ball is twice the diameter of its respective said wire.

9. The steerable catheter assembly according to claim 8, wherein each of said wires has a diameter of 0.010", and each said steel balls has a diameter of 0.020".

10. The steerable catheter assembly according to claim 8, wherein said each ballized wire further includes a jacket securely fixed thereabout.

11. The steerable catheter assembly according to claim 10, wherein said jacket is manufactured from U.V curable epoxy glue injected around each of said wires.

12. The steerable catheter assembly according to claim 8, wherein said ballized wire further includes a washer securely fixed about said wire adjacent to said steel ball.

13. The steerable catheter assembly according to claim 12, wherein said washer has an outside diameter of 0.024" and an inside diameter of 0.012", where said washer is slid over said ballized wire and positioned adjacent to said steel ball, and that said washer and said steel ball are pulled into said lumen extrusion shaft through said minor opening.

14. The steerable catheter assembly according to claim 8, wherein said ballized wire further includes a wire eyelet securely fixed thereabout adjacent said steel ball.

15. The steerable catheter assembly according to claim 14, wherein said wire eyelet has an outside diameter of 0.024" and an inside diameter of 0.012", where said wire eyelet is slid over said ballized wire and positioned adjacent to said steel ball.

16. The steerable catheter assembly according to claim 8, wherein said ballized wire further includes a wire spring securely fixed thereabout adjacent to said steel ball.

17. The steerable catheter assembly according to claim 1 wherein a first said luer lock comprises a fastening means removably attached to said second end.

18. The steerable catheter assembly according to claim 1, wherein said major tubing members extend between said luer locks and said manifold.

* * * * *